United States Patent
Schreck

(10) Patent No.: US 11,571,291 B2
(45) Date of Patent: Feb. 7, 2023

(54) PERCUTANEOUS METHOD AND DEVICE TO TREAT DISSECTIONS

(71) Applicant: Endologix LLC, Irvine, CA (US)

(72) Inventor: Stefan G. Schreck, Fallbrook, CA (US)

(73) Assignee: Endologix LLC, Irvine, CA (US)

( * ) Notice: Subject to any disclaimer, the term of this patent is extended or adjusted under 35 U.S.C. 154(b) by 336 days.

(21) Appl. No.: 16/992,020

(22) Filed: Aug. 12, 2020

(65) Prior Publication Data

US 2020/0368010 A1 Nov. 26, 2020

Related U.S. Application Data

(63) Continuation of application No. 15/429,090, filed on Feb. 9, 2017, now Pat. No. 10,772,717, which is a
(Continued)

(51) Int. Cl.
*A61F 2/06* (2013.01)
*A61B 17/12* (2006.01)
(Continued)

(52) U.S. Cl.
CPC ............ *A61F 2/06* (2013.01); *A61B 17/0057* (2013.01); *A61F 2/07* (2013.01); *A61B 17/12031* (2013.01);
(Continued)

(58) Field of Classification Search
CPC ........ A61B 17/12099; A61B 17/12109; A61B 17/12113; A61B 17/12118; A61F 2/06; A61F 2/07; A61F 2/958; A61F 2/966; A61F 2002/821; A61F 2002/067; A61F 2220/0016; A61F 2220/0008; A61F 2230/0008; A61F 2250/006
See application file for complete search history.

(56) References Cited

U.S. PATENT DOCUMENTS 6,231,597 B1  5/2001  Deem et al.
6,309,367 B1  10/2001  Boock
(Continued)

FOREIGN PATENT DOCUMENTS

WO    WO-01/74273 A1    10/2001
WO    WO-01/87184 A1    11/2001
WO    WO-01/93782 A1    12/2001

OTHER PUBLICATIONS

European Office Action dated Jun. 7, 2013, from application No. 10716999.7.
(Continued)

*Primary Examiner* — Diane D Yabut
(74) *Attorney, Agent, or Firm* — Foley & Lardner LLP

(57) ABSTRACT

Some embodiments are directed to methods and systems for percutaneously treating dissections in a patient's vasculature, such as, without limitation, the aorta. The method can include deploying a catheter containing a collapsed anchoring element, frame, and cover through a first vessel to an entry point of the dissection. The anchoring element can be secured to the second branch vessel. The frame can be expanded in the first branch vessel. The cover can be unfolded over at least a portion of the entry point. The cover then reduces blood flow into the entry point.

15 Claims, 19 Drawing Sheets

Related U.S. Application Data continuation of application No. 12/771,711, filed on Apr. 30, 2010, now Pat. No. 9,579,103.

(60) Provisional application No. 61/174,888, filed on May 1, 2009.

(51) Int. Cl.
*A61F 2/07* (2013.01)
*A61B 17/00* (2006.01)
*A61F 2/958* (2013.01)
*A61F 2/966* (2013.01)

(52) U.S. Cl.
CPC ... *A61B 17/12036* (2013.01); *A61B 17/12109* (2013.01); *A61B 17/12172* (2013.01); *A61B 2017/0061* (2013.01); *A61B 2017/00575* (2013.01); *A61B 2017/1205* (2013.01); *A61F 2/958* (2013.01); *A61F 2/966* (2013.01); *A61F 2002/067* (2013.01); *A61F 2220/0008* (2013.01); *A61F 2220/0016* (2013.01); *A61F 2230/0008* (2013.01); *A61F 2250/006* (2013.01)

(56) References Cited

U.S. PATENT DOCUMENTS

| | | |
|---|---|---|
| 6,368,355 B1 | 4/2002 | Uflacker |
| 2002/0013618 A1 | 1/2002 | Marotta et al. |
| 2006/0178726 A1 | 8/2006 | Douglas |
| 2007/0038283 A1* | 2/2007 | Mustapha ............... A61F 2/856 623/1.11 |
| 2007/0088387 A1 | 4/2007 | Eskridge et al. |
| 2007/0168013 A1 | 7/2007 | Douglas |
| 2008/0114436 A1 | 5/2008 | Dieck et al. |
| 2008/0221600 A1 | 9/2008 | Dieck et al. |
| 2009/0018635 A1 | 1/2009 | Holman et al. |
| 2009/0018638 A1 | 1/2009 | Shirley et al. |
| 2009/0228029 A1 | 9/2009 | Lee |
| 2009/0264914 A1 | 10/2009 | Riina et al. |
| 2010/0094335 A1 | 4/2010 | Gerberding et al. |

OTHER PUBLICATIONS

Final Office Action dated Jul. 12, 2016, from U.S. Appl. No. 12/771,711.
Final Office Action dated Mar. 12, 2015, from U.S. Appl. No. 12/771,711.
Final Office Action dated Nov. 23, 2012, from U.S. Appl. No. 12/771,711.
Final Office Action dated Oct. 23, 2019, from U.S. Appl. No. 15/429,090.
International Search Report and Written Opinion re PCT/US2010/033274, filed Apr. 30, 2010, dated Dec. 30, 2010.
Non-final Office Action dated Apr. 3, 2012, from U.S. Appl. No. 12/771,711.
Non-final Office Action dated Dec. 15, 2015, from U.S. Appl. No. 12/771,711.
Non-Final Office Action dated Feb. 6, 2020, from U.S. Appl. No. 15/429,090.
Non-Final Office Action dated Mar. 21, 2019, from U.S. Appl. No. 15/429,090.
Non-final Office Action dated Sep. 10, 2014, from U.S. Appl. No. 12/771,711.
Notice of Allowance dated May 14, 2020, from U.S. Appl. No. 15/429,090.
Notice of Allowance dated Oct. 17, 2016, from U.S. Appl. No. 12/771,711.

* cited by examiner

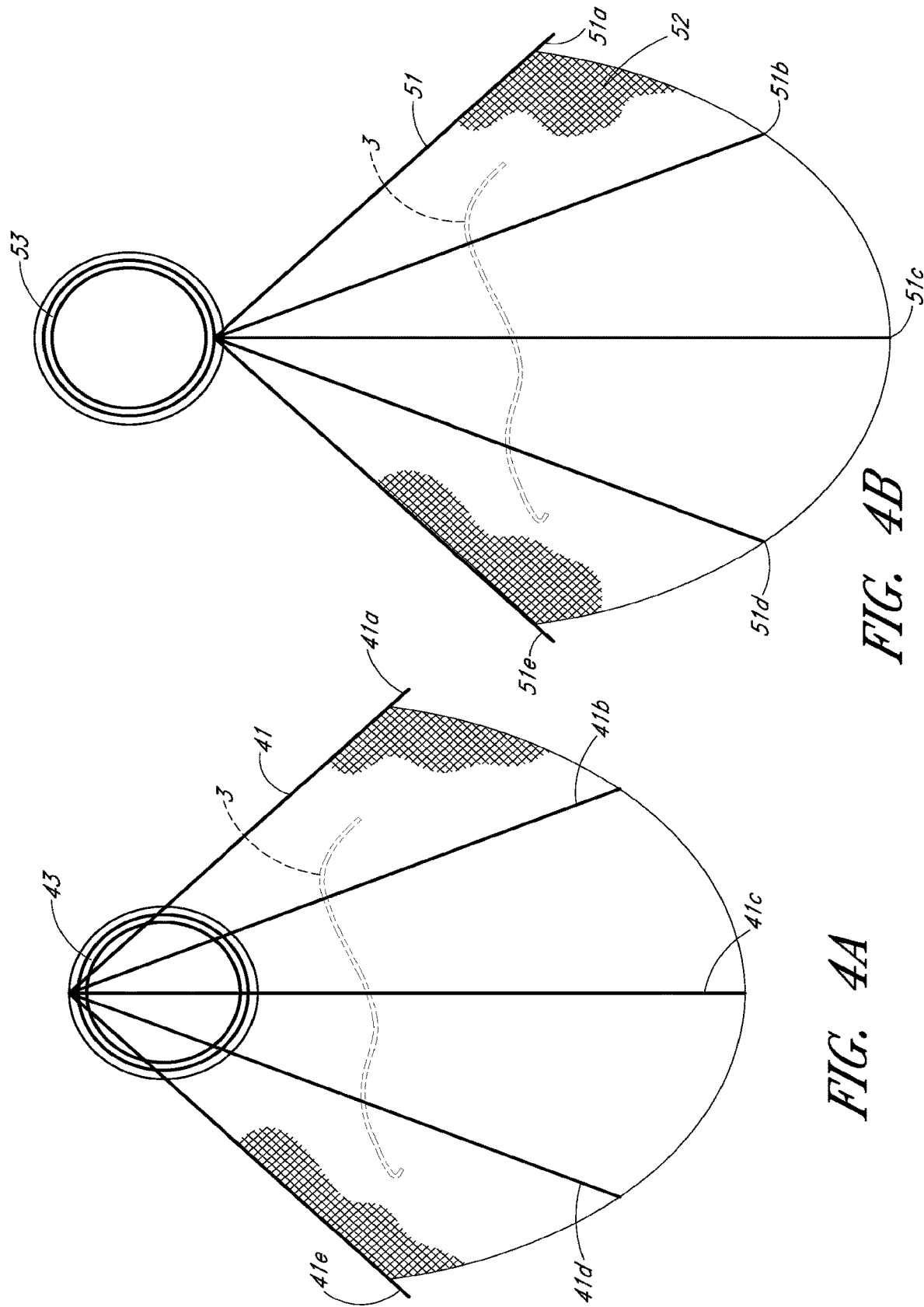

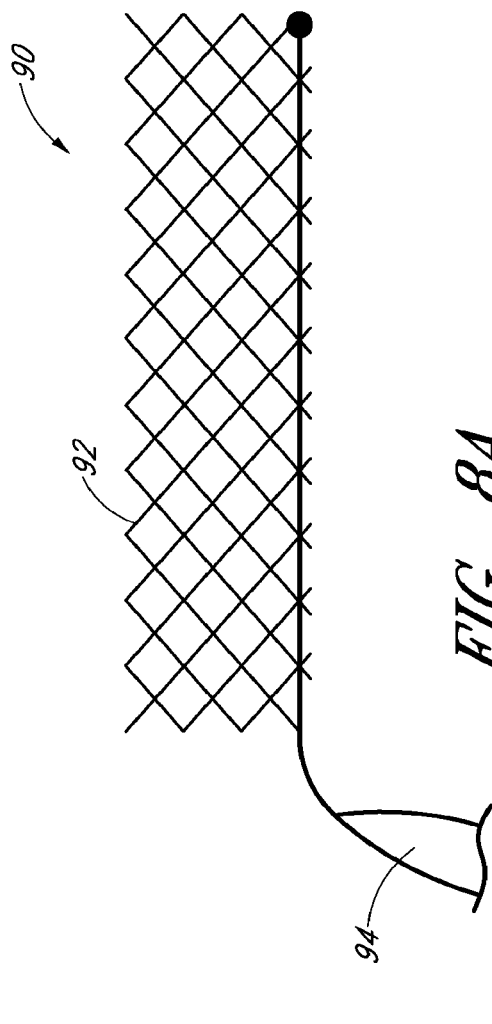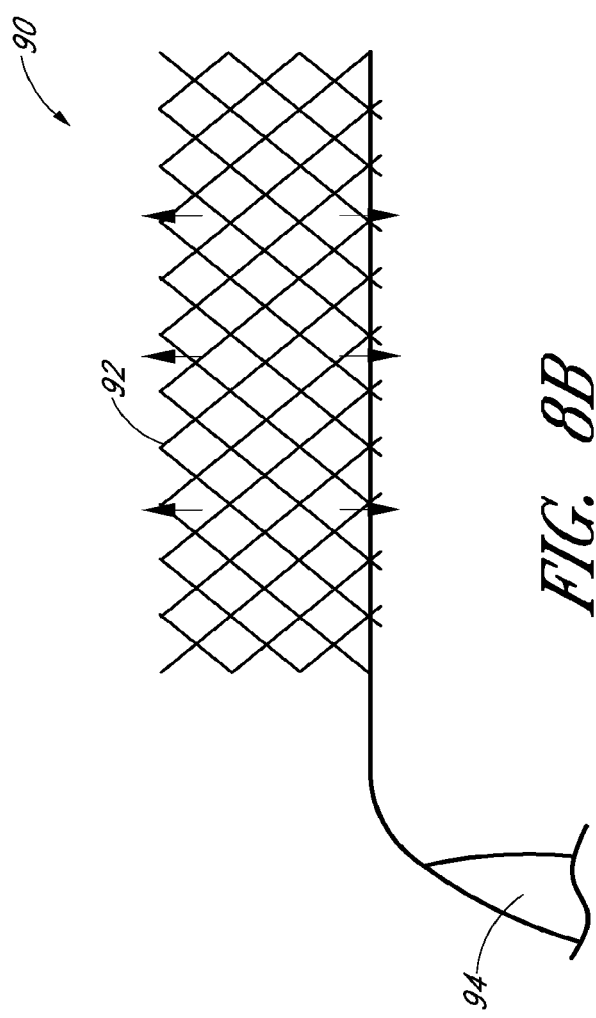

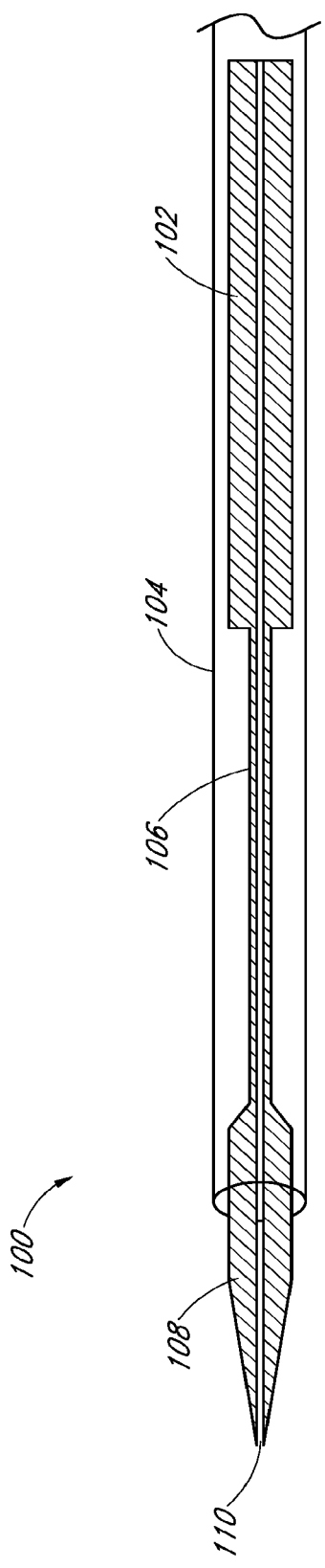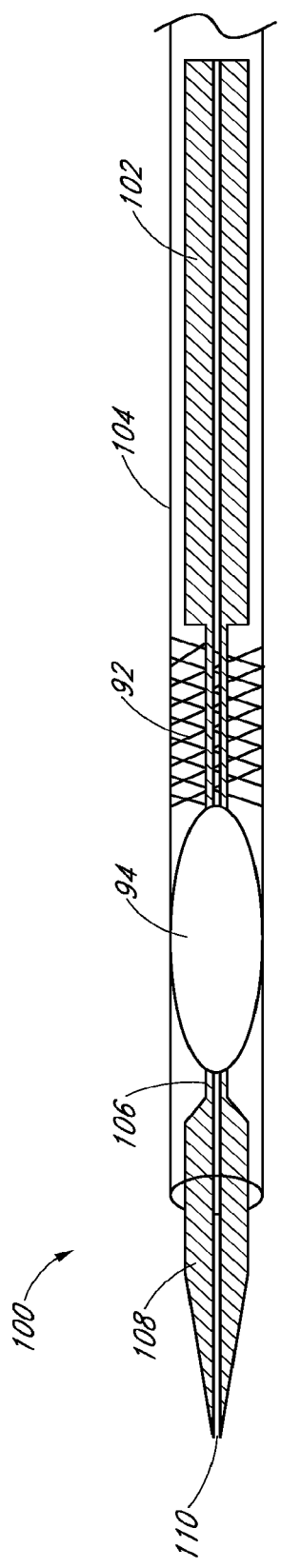
FIG. 9A
FIG. 9B

PERCUTANEOUS METHOD AND DEVICE TO TREAT DISSECTIONS

PRIORITY INFORMATION AND INCORPORATION BY REFERENCE

This application is a continuation of U.S. patent application Ser. No. 15/429,090, filed Feb. 9, 2017, which is a continuation of U.S. patent application Ser. No. 12/771,711, filed Apr. 30, 2010, now U.S. Pat. No. 9,579,103, granted Feb. 28, 2017, which claims the benefit of U.S. Provisional Patent Application No. 61/174,888, filed on May 1, 2009, the entire content of which is hereby incorporated by reference and should be considered part of this specification. Additionally, U.S. patent application Ser. No. 12/101,863, filed on Apr. 11, 2008 (entitled "Bifurcated Graft Deployment Systems And Methods") is also hereby incorporated by reference in its entirety as if fully set forth herein.

BACKGROUND OF THE DISCLOSURE

The present disclosure relates to a method and device for the treatment of aortic dissections.

BACKGROUND OF THE DISCLOSURE

An aortic dissection is a dangerous condition with high mortality rates. In an aortic dissection, a tear typically develops in the intima of the aorta that propagates along the vessel wall delaminating the inner layer of the aorta from the outer layer. Blood enters the space between the layers creating a false lumen. Several additional tears or entry points can be created between the true lumen of the aorta and the false lumen. In the acute phase, dissections may close a perfusion from the aorta to vital organs. In the chronic phase, the weakened tissue can develop into an aneurysm and ultimately rupture. Dissections involving the ascending aorta are referred to as Type A dissections. Dissections only involving the descending aorta are referred to as Type B dissections.

Current treatments for dissections include medical management to lower the blood pressure of the patient and reduce the hemodynamic stresses on the diseased vessel. If dissections are symptomatic, surgical intervention is necessary. Portions of the diseased aorta are replaced by a surgical graft and the dissection flap is reattached. More recently, stent grafts have been used to close the primary entry point into the false lumen with the goal to thrombose the false lumen and maintain patency of the true lumen.

Endovascular treatment of aortic dissections with a thoracic aortic stent graft may risk inter-operative and post-operative complications. The catheter delivery systems of thoracic stent grafts typically have a profile of 20-24 Fr, requiring a cut-down or conduit for delivery. Vessel damage by the large delivery catheters is common. Stent grafts are difficult to deploy accurately in the thoracic aorta due to the high blood flow through the thoracic aorta. The proximal end of the stent graft, particularly uncovered stent sections, may cause the dissection tear to propagate proximally into the aortic arch.

There is a clear need for an improved method to treat aortic dissections. The current application describes certain embodiments, which provide a solution to the treatment of aortic dissections while minimizing the impact on the aorta.

SUMMARY OF SOME EMBODIMENTS

Some embodiments of the present disclosure are directed to methods for treating a vascular dissection, comprising advancing a catheter comprising a cover and a collapsed anchoring element connected to a frame through a first vessel to an entry point of the dissection, securing the anchoring element to a second vessel that is in communication with the first vessel, expanding the frame in the first vessel, and unfolding and positioning the cover over at least a portion of the entry point. In some embodiments, the cover can reduce blood flow into the entry point.

Some embodiments are directed to methods for treating a vascular dissection, comprising advancing a catheter supporting a prosthesis to an entry point of the dissection, wherein the entry point of the dissection is located in a first vessel and the prosthesis comprises a cover and a collapsible anchoring element in communication with the cover, securing the anchoring element to a second vessel that is in communication with the first vessel, expanding the cover in the first vessel, and positioning the cover over at least a portion of the entry point of the dissection. In some embodiments, the cover can be configured to reduce blood flow into the entry point of the dissection.

Some embodiments are directed to a device for treating vascular dissections, comprising an anchoring element, a frame supported by the anchoring element, and a cover supported by the frame. The cover can be configured to cover a portion of a wall of a first vessel over an entry point into the dissection to at least substantially reduce blood flow into the entry point. The anchoring element can be configured to be supported by a second vessel in communication with the first vessel. Some embodiments are directed to a device for treating vascular dissections, comprising an anchoring element and a cover supported by the anchoring element, wherein the cover is configured to cover only a portion of a wall of a first vessel over an entry point into the dissection and is configured to at least substantially reduce blood flow into the entry point, and the anchoring element is configured to be deployed within a second vessel in communication with the first vessel.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

FIGS. 4A and 4B illustrate another embodiment of a device to treat dissections.

FIGS. 8A and 8B are schematic side view representations of an embodiment of a device to treat dissections, wherein a support member is shown in a collapsed state in FIG. 8A and an expanded state in FIG. 8B.

FIG. 9A is a partial section schematic view of an embodiment of a delivery catheter that can be used to deploy some embodiments of the devices to treat dissections disclosed herein.

FIG. 9B is a partial section schematic view of the embodiment of the delivery catheter shown in FIG. 9A, showing an embodiment of a device to treat dissections supported therein.

DETAILED DESCRIPTION OF SOME EXEMPLIFYING EMBODIMENTS

Some embodiments of the present application pertain to methods of treating aortic dissections. Specifically, without limitation, these methods may be well suited for the treatment of acute Type B dissections involving the descending aorta, or for the treatment of dissections or tears anywhere in a human or animal vasculature.

Current devices used for the endovascular treatment of dissections are aortic stent grafts that require delivery systems of 20-24 Fr. These stent grafts rely on a large diameter stent for anchoring in the aorta and have a graft that covers the complete circumference of the aorta.

By anchoring the device in a branch vessel, as in some embodiments of this disclosure, the need for an aortic stent is removed. By covering only the flap of the dissection, as in some embodiments disclosed herein, less covering material is necessary. Some embodiments of the prosthesis, as described in greater detail below, can be delivered in a low-profile catheter of less than 12 Fr, or, in some embodiments, less than 8 Fr. Furthermore, the device can be directly delivered from the branch vessel.

Some embodiments herein relate to devices and methods for creating a thrombosis in the false lumen of a dissection by closing the primary entry point of the dissection with a patch or a cover instead of a stent graft. In Type B dissections, the primary entry point is typically located at the transition region from the aortic arch to the descending thoracic aorta, distal to the subclavian artery. In some embodiments disclosed herein, a patch can be positioned over the entry point of the dissection. The patch can be, for example and without limitation, anchored in or secured to the subclavian artery. For example, in some embodiments, the radial artery can be punctured to deliver the device into the subclavian artery. In situations where the entry point to the dissection is located at a different section of the aorta, other branch vessels may be utilized for anchoring the device. In some embodiments, the patch can be configured so as to not cover the entire inner surface of the blood vessel, such as, but not limited to, the aorta, but can, rather, cover only a portion of the wall of the blood vessel.

Figure 1:
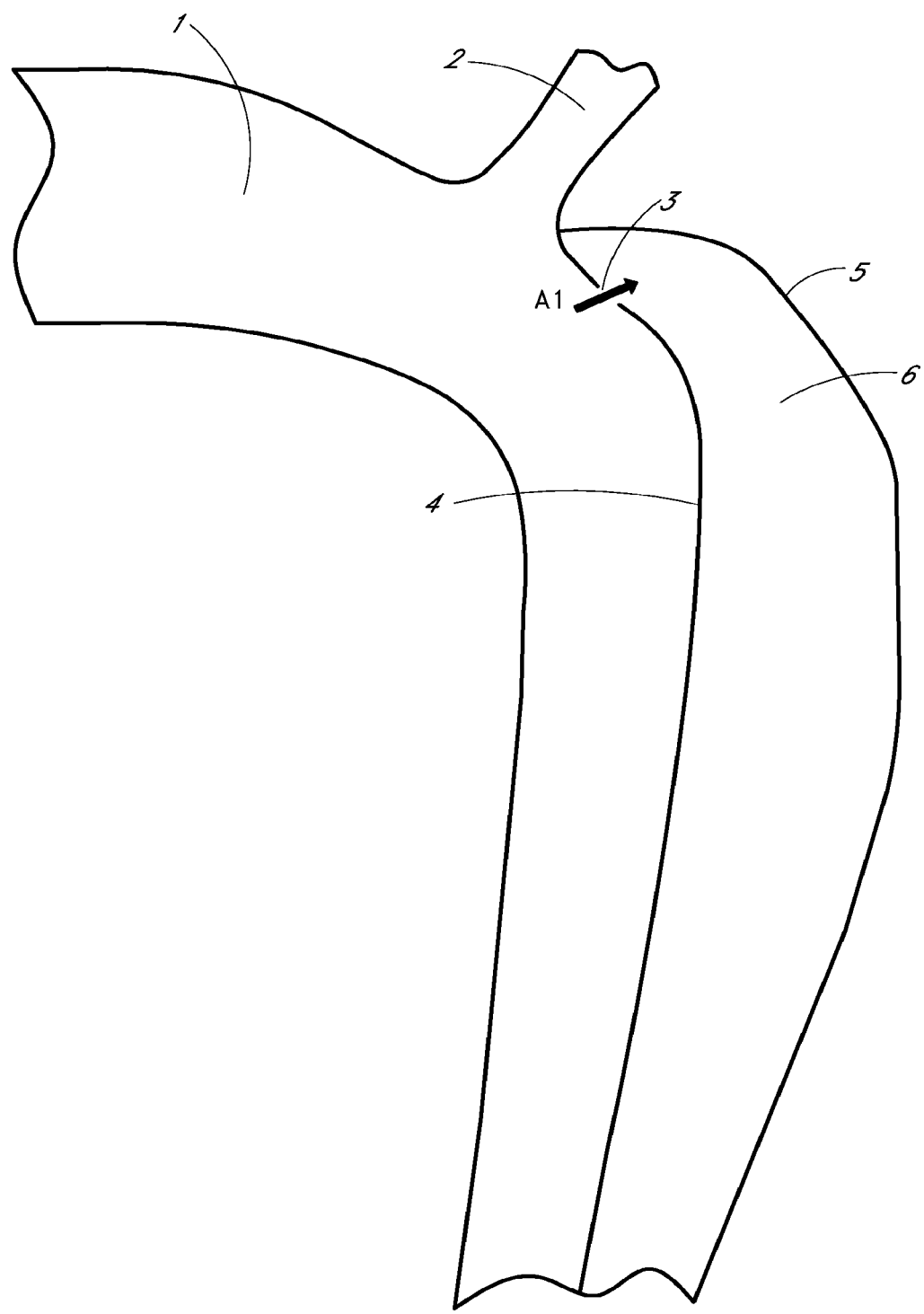
FIG. 1 is a schematic illustration of a type B dissection in the aorta.

FIG. 1 is a schematic illustration of a type B dissection in the aorta. A tear or entry point 3 in the inner layer of the aorta 1 distal to the subclavian artery 2 can be severe enough to allow blood to enter into the aortic wall and peel the inner layer 4 of the aorta from the outer layer 5. Arrow A1 in FIG. 1 represents the flow of blood into the aortic wall. The space created by the blood between the two layers is referred to as the false lumen 6. The tear 3 is referred to as the entry point to the false lumen. The separated inner layer 4 is referred to as the flap. In some embodiments, the dissection is treated by closing the entry point so that the blood cannot enter and pressurize the false lumen 6.

Figures 2A, 2B:
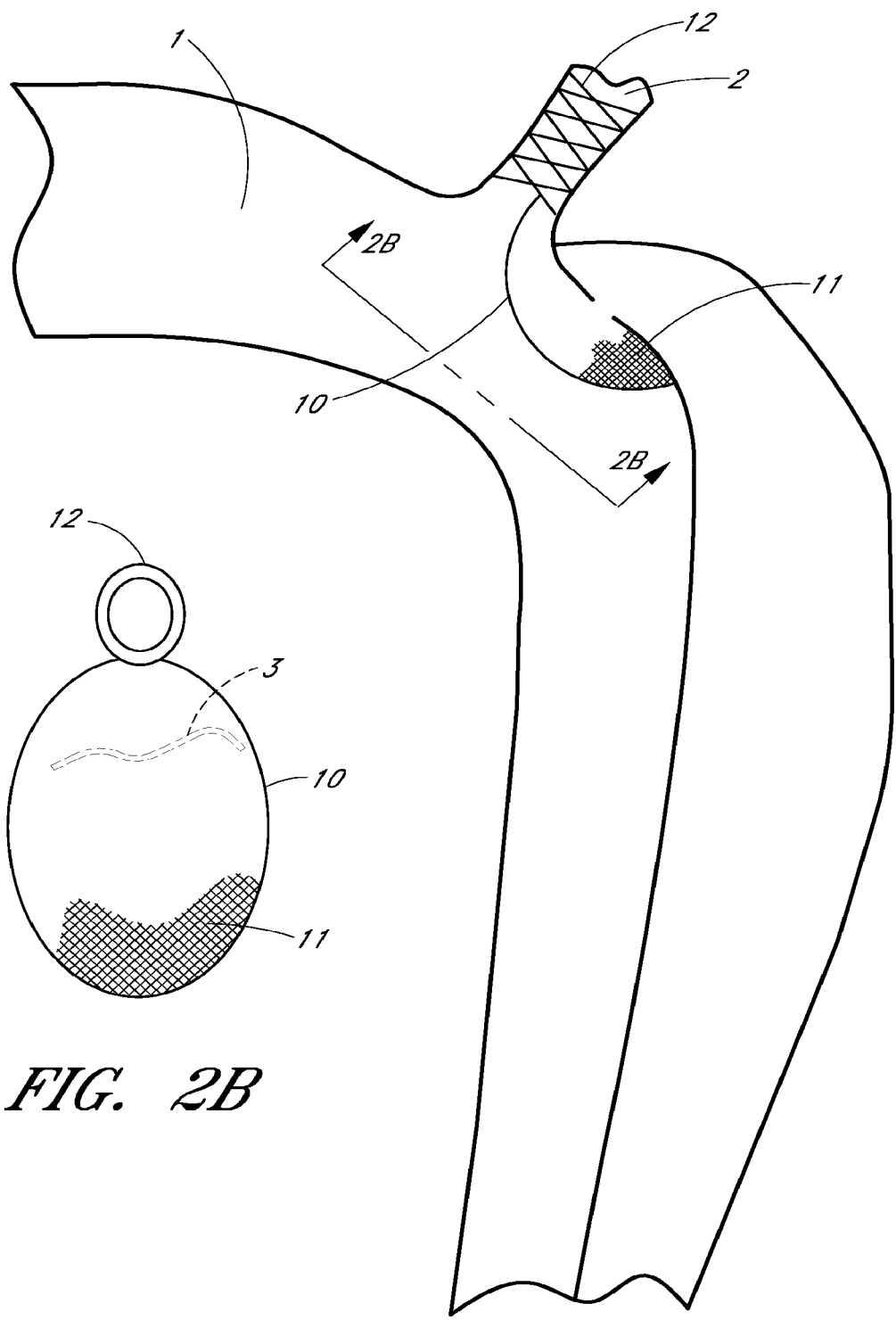
FIG. 2A illustrates an embodiment of a device to treat dissections.
FIG. 2B is a schematic illustration of the embodiment of the treatment device illustrated in FIG. 2A, taken along line 2B-2B in FIG. 2A.

FIGS. 2A and 2B show an embodiment of a treatment device to substantially or fully close the entry point of a type B dissection in the aorta. In some embodiments, the device or prosthesis can comprise a cover 11 and a support member or anchoring element 12. In some embodiments, the cover 11 or any cover of any other device or prosthesis embodiment disclosed herein can be sufficiently rigid to be self-supporting within the target vessel after being deployed. In some embodiments, however, as in the illustrated embodiment, the device can have a collapsible frame 10 configured to support the cover 11. In some embodiments, the cover 11 or any other cover disclosed herein can be configured to have an integral frame or support structure such that an additional frame is not required. Additionally, some embodiments of the cover or the frame disclosed herein, including without limitation cover 11 and frame 10, can be biased or otherwise be configured to deflect or move against or adjacent to the vessel wall at the location of the entry point to the dissection upon deployment from a suitable delivery device.

The device can be collapsed into a low-profile delivery catheter for percutaneous delivery to the treatment site. Preferably, the device can be delivered from the radial artery or the femoral artery. The collapsible frame 10 can be made from a shape memory material, including, without limitation, Nitinol. In some embodiments, the shape of the frame 10 can be elliptical to conform to the aortic wall. The cover 11 can be suspended in the frame 10.

In some embodiments, the cover 11 can be made from a biocompatible, flexible, thin material. Potential materials include, but are not limited to, polyester, ePTFE, polyurethane, silk, animal tissue or any other materials suitable for long-term implants. In some embodiments, the cover 11 can be made from a material that promotes or assists tissue repair and integration of the cover 11 into the aortic wall. In some embodiments, the cover 11 can be made from matrices designed to act as a scaffold for tissue-engineered grafts. The cover 11 can comprise proteins such as, without limitation, collagen and elastin, which are natural building blocks of the extracellular matrix in the aortic wall.

In some embodiments, the cover 11 can comprise fibrin, polysaccharides, like chitosan or glycosaminoglycans. In some embodiments, the proteins can be cross-linked by a suitable cross-linking agent. Suitable cross-linking agents can include, without limitation, glutaraldehydes, carbodiimide, tannins, polyphenols, and photo-activated crosslinking agents. In some embodiments, the protein layer can be harvested from mammals. Possible sources of mammalian protein layers include, without limitation, pericardium, small intestine submucosa, blood vessels, and skin.

In some embodiments, the thickness of the cover 11 can range from approximately 0.0001 inches to approximately 0.01 inches. In some embodiments, the thickness of the cover 11 can be from approximately 0.0005 inches to approximately 0.0020 inches. The cover 11 can be made from non-porous materials, porous materials, a mesh, or from knitted or woven fibers. In some embodiments, the biochemical and surface properties of the cover 11 can promote adhesion of the cover to the aortic wall. For example, the cover 11 can be made from a knitted polyester or silk fabric. The cover 11 can be attached to the frame 10 with sutures, adhesive, or with any other suitable fasteners or techniques. In some embodiments, the cover 11 can be molded directly onto the frame.

The frame 10 can move from a collapsed state during deployment to an expanded state after deployment into the aorta. In some embodiments, the frame 10 can unfold the cover 11 during deployment. The blood flow can push the cover against the aortic wall, thus helping to secure the cover 11 at the target location. The flexible cover 11 can conform to the wall of the aorta 1 and can seal off the entry point 3. To prevent migration of the cover 11, the frame 10 can be connected to an anchoring element 12 that can be placed in a side branch of the aorta, preferably the subclavian artery 2. The anchoring element 12 can be placed in any suitable branch vessel of the aorta, including without limitation the carotid or brachiocephalic artery. The anchoring element 12 or any other anchoring element or support member can be a self-expandable stent, balloon-expandable stent, coil, hook, barb, balloon, stent graft, screw, staple, or other similar or suitable device.

Figure 3B:
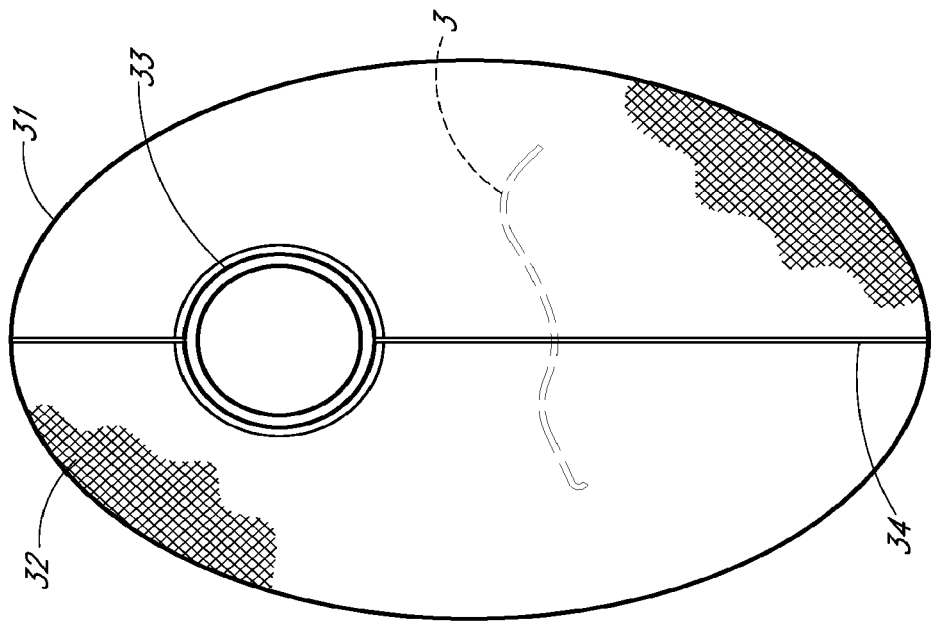
FIGS. 3A and 3B illustrate another embodiment of a device to treat dissections.
Figure 3A:
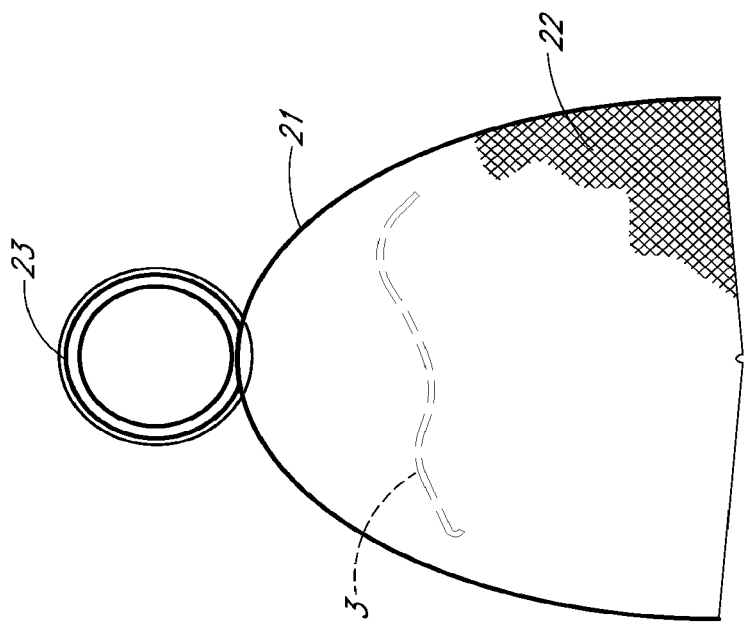

FIGS. 3A and 3B illustrate another embodiment of a device to treat dissections. With reference to FIG. 3A, in some embodiments, the cover 22 can have a half-circular or ovular shape. The frame 21 can comprise an arcuately-shaped wire. In some embodiments, the cover 22 can be unsupported at the distal end. In FIG. 3B, a further alternative embodiment of the cover 32 is shown. As shown therein, some embodiments of the cover 32 can extend proximally beyond the anchoring element 33, which may be suitable for situations in which the entry point 3 is at or proximal to the subclavian artery. The subclavian artery can be covered by the cover 32. In some embodiments, the cover 32 can have an opening to allow blood to enter into the subclavian artery. In some embodiments, the frame 31 can have an additional central strut 34 support the cover 31 or to push the cover 31 against the aortic wall.

FIGS. 4A and 4B illustrate another embodiment of a device to treat dissections. With reference to FIG. 4A, the device can have one or more supports 41a-e that can be connected to the anchoring element 43. The supports 41a-e can be supported on one end by the proximal end of the anchoring element 43. Alternatively, the supports 51a-e can be supported by the distal end of anchoring element 53 as shown in FIG. 4B.

Figure 5:
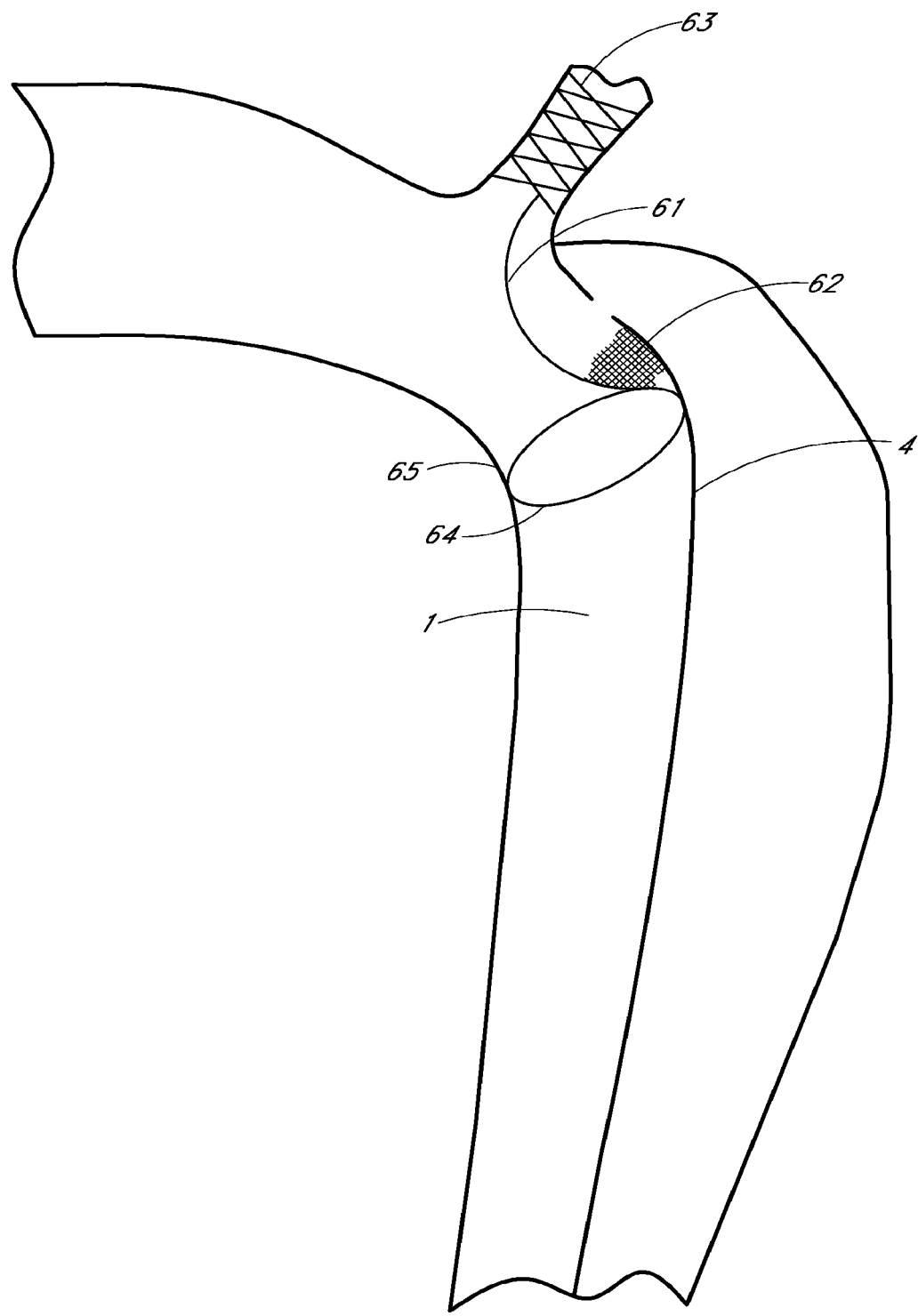
FIG. 5 illustrates another embodiment of a device to treat dissections.

FIG. 5 illustrates another embodiment of a device to treat dissections, configured to substantially or fully close the entry point of a type B dissection in the aorta. In some embodiments, the device can be similar to that shown in FIG. 2. In some embodiments, a support element 64 can be connected to the distal end of the frame 61. In some embodiments, the support element 64 can push the frame 61 and cover 62 against the flap 4 of the dissection. The support element 64 can have an elliptical shape and can be made from a similar material as the frame 61. The ellipse can be slightly larger than the diameter of the aorta 1 so that the support element 64 can be in contact with the flap 4 and the opposing aortic wall 65. The support element 64 can be comprised to support a distal portion of the frame 61 so as to prevent or inhibit the distal portion of the cover 62 from detaching or moving away from the flap 4.

Figures 6A, 6B:
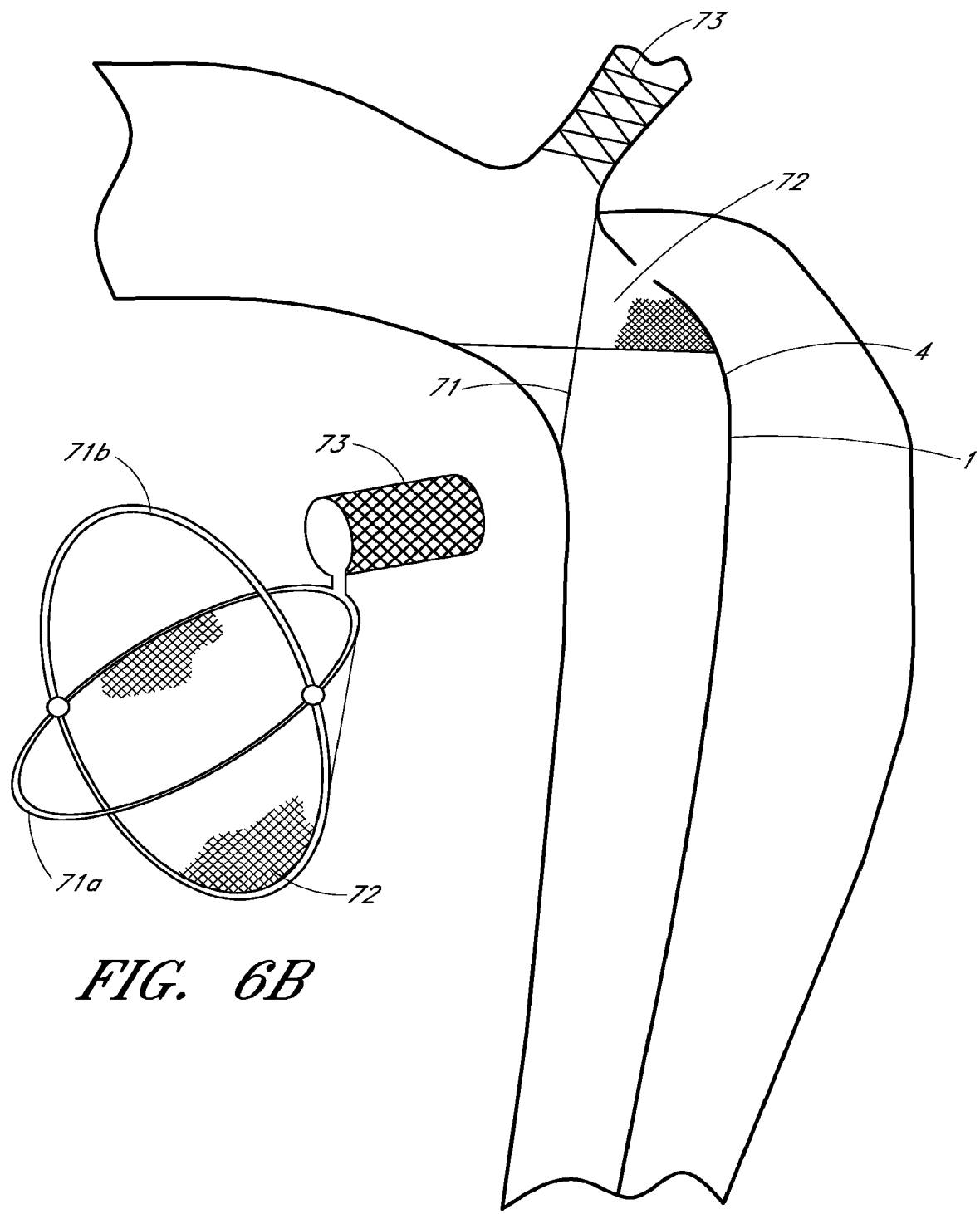
FIGS. 6A and 6B illustrate another embodiment of a device to treat dissections.

FIGS. 6A and 6B illustrate another embodiment of a device configured to substantially or fully close the entry point of a type B dissection in the aorta. In some embodiments, the frame 71 can comprise two elliptical elements 71a and 71b that can form an open cage. The cover 72 can be configured to conform to or be supported by one half of the frame 71. When placed in the aorta 1, some embodiments of the frame can prevent the cover 72 from detaching or moving away from the flap 4. Further, some embodiments of the frame can conform to the local cross-sectional area of the aorta.

Figures 7A, 7B:
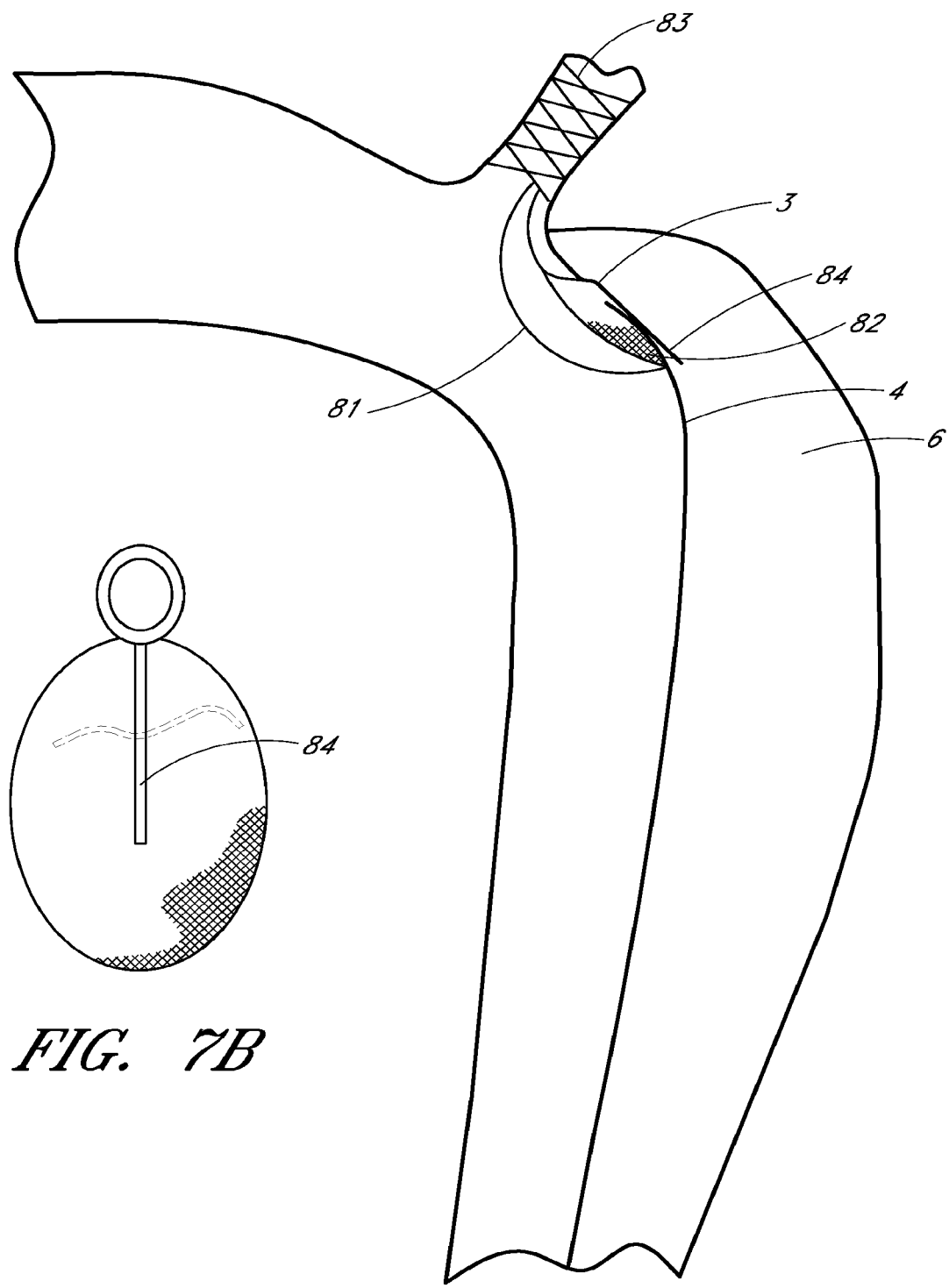
FIGS. 7 A and 7B illustrate another embodiment of a device to treat dissections.

FIGS. 7A and 7B illustrate another embodiment of a device to substantially or fully close the entry point of a type B dissection in the aorta. In some embodiments, the device can be similar to the device shown in FIG. 2, except as described below. A support element 84 can be supported by the anchor element 81. The support element 84 can be advanced through the entry point 3 into the false lumen 6 and can support the frame 81 from within the false lumen 6. The frame 81 and the support element 84 can effectively sandwich the flap 4 and can prevent the cover 82 from detaching from the flap 4. In some embodiments, the frame 81 or the support element 84 can perform a clip-like function.

FIGS. 8A and 8B are schematic side view representations of an embodiment of a device 100 to treat dissections, wherein a support member 92 is shown in a collapsed state in FIG. 8A and an expanded state in FIG. 8B. The device 100 can have any of the same features, components, or other details of any other embodiments of the devices to treat dissections disclosed herein. Accordingly, the support member 92 (also referred to as an anchor member herein) can be any suitable stent, including without limitation a self-expandable, balloon expandable stent, or any other anchoring element disclosed herein that can be deployed in a vessel that is adjacent to the vessel having the dissection therein. The support member 92 can be collapsed during delivery and expanded once the support member 92 is positioned in the target vessel location. As illustrated therein, a cover member 94 can be attached to the support member 92 and can be configured to substantially or completely cover the entry point to the dissection.

FIG. 9A is a partial section schematic view of a delivery catheter 100 that can be used to deploy some embodiments of the devices to treat dissections disclosed herein, such as without limitation the device 90 described above. In some embodiments, the delivery catheter 100 can have any or any combination of the features, components, or other details of the delivery catheter embodiments disclosed in U.S. application Ser. No. 12/101,863, filed on Apr. 11, 2008 and entitled "Bifurcated Graft Deployment Systems And Methods," which application is hereby incorporated by reference as if fully set forth herein.

With reference to FIG. 9A, the delivery catheter 100 can have an inner core 102 that can extend from a proximal end of the delivery catheter 100 through a lumen in an outer sheath 104. The inner core 102 can be axially and rotationally movable within the outer sheath 104. A tube member 106 can extend from a distal end portion of the inner core 102 and can support an atraumatic distal tip 108. A guidewire lumen 110 can be formed through the axial centerline of the distal tip 108, the tube member 106, and the inner core 102.

FIG. 9B is a partial section schematic view of the delivery catheter shown in FIG. 9A, showing the embodiment of the device 90 to treat dissections supported therein. In some embodiments, the outer sheath 104 can be used to restrain the anchoring member 92 and the cover 94, both of which can be supported within the delivery catheter 100 in a collapsed configuration. Additionally, in some embodiments, although not required, a frame member can be attached to the anchoring member 92 and can be used to support the cover 106. The device 100 can be supported by the tube member 106 and radially restrained by the outer sheath 104 and, as will be described. As will be described, the radial restraint can be removed by retracting the outer sheath 104 relative to the inner core 102, thereby exposing the device 100.

Figure 10:
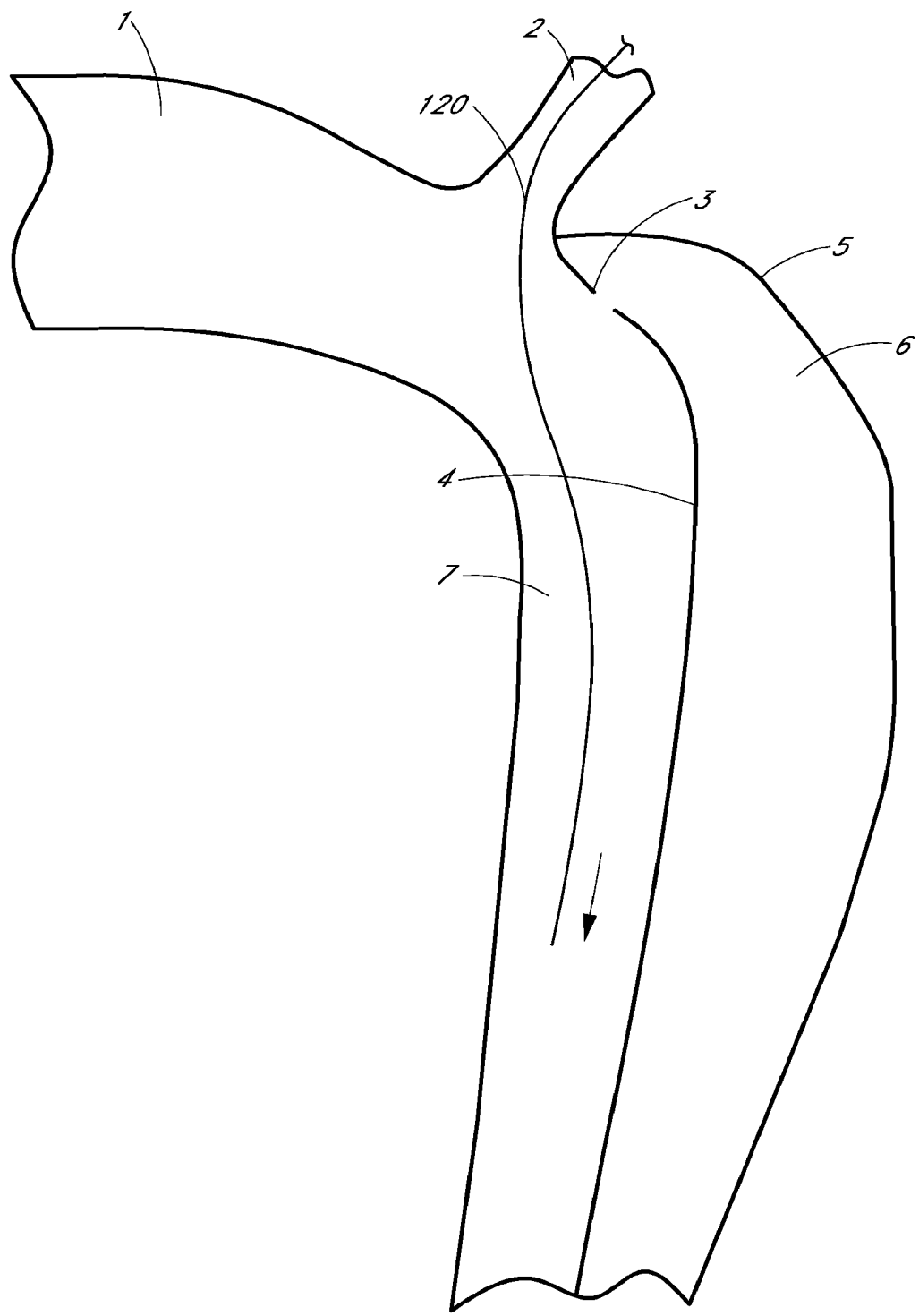
FIG. 10 is a schematic illustration of patient's aorta having a type B dissection therein, showing a guidewire being advanced through a patient's subclavian artery into the aorta.
Figure 11:
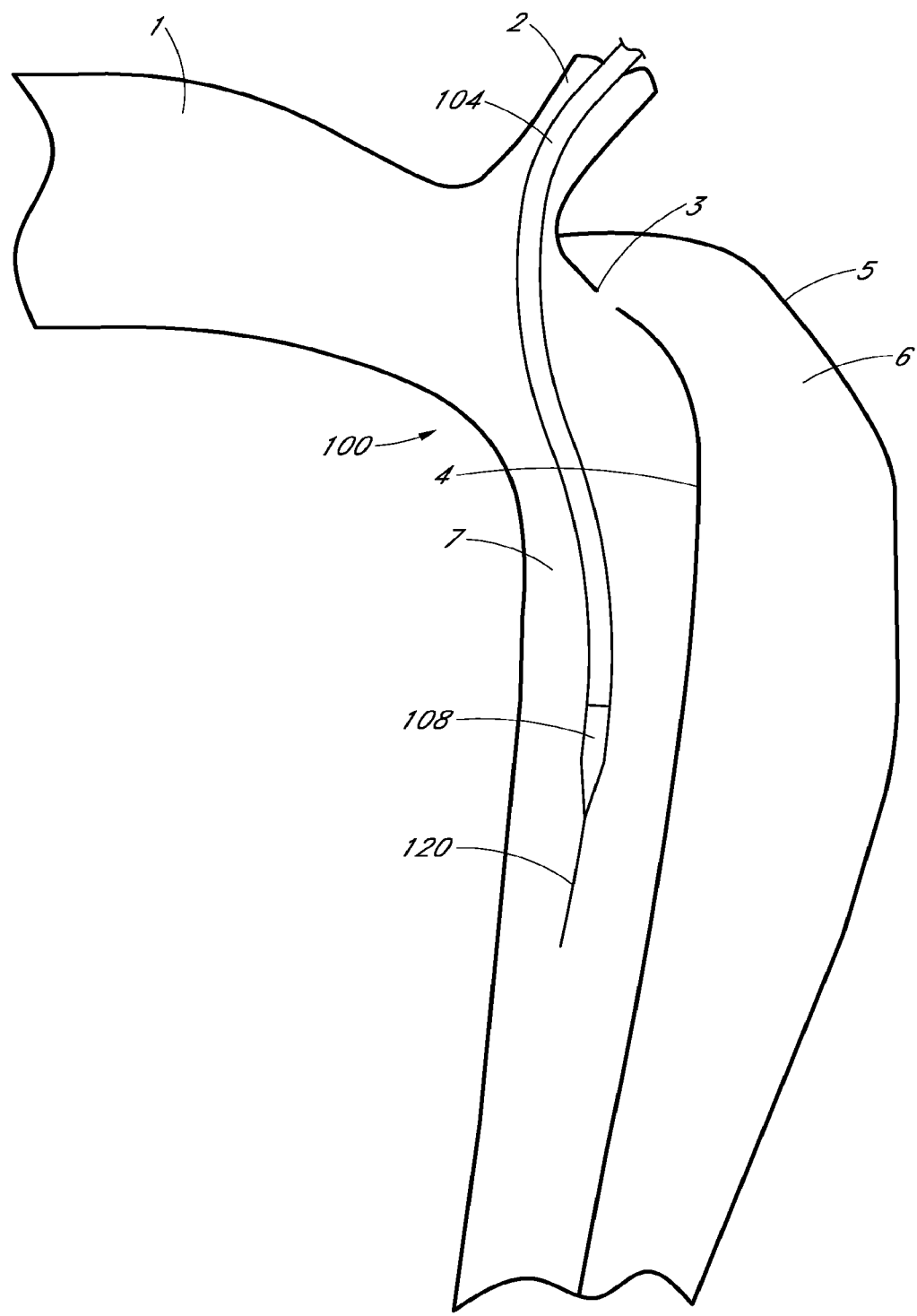
FIG. 11 is a schematic illustration showing an embodiment of a delivery catheter being advanced over the guidewire of FIG. 10.

With the foregoing description, several arrangements of methods to deploy a device to treat a dissection will be described. With reference to FIG. 10, which is a schematic illustration of patient's aorta having a type B dissection therein, a guidewire 120 can be advanced through a patient's subclavian artery 2 into the aorta 7. In some embodiments, the guidewire can be advanced into the subclavian artery 2 through a patient's radial artery. FIG. 11 is a schematic illustration showing the delivery catheter 100 being advanced over the guidewire 120. In this arrangement, the delivery catheter 100 can be advanced through a patient's radial artery into the subclavian and aortic arteries.

Figure 12:
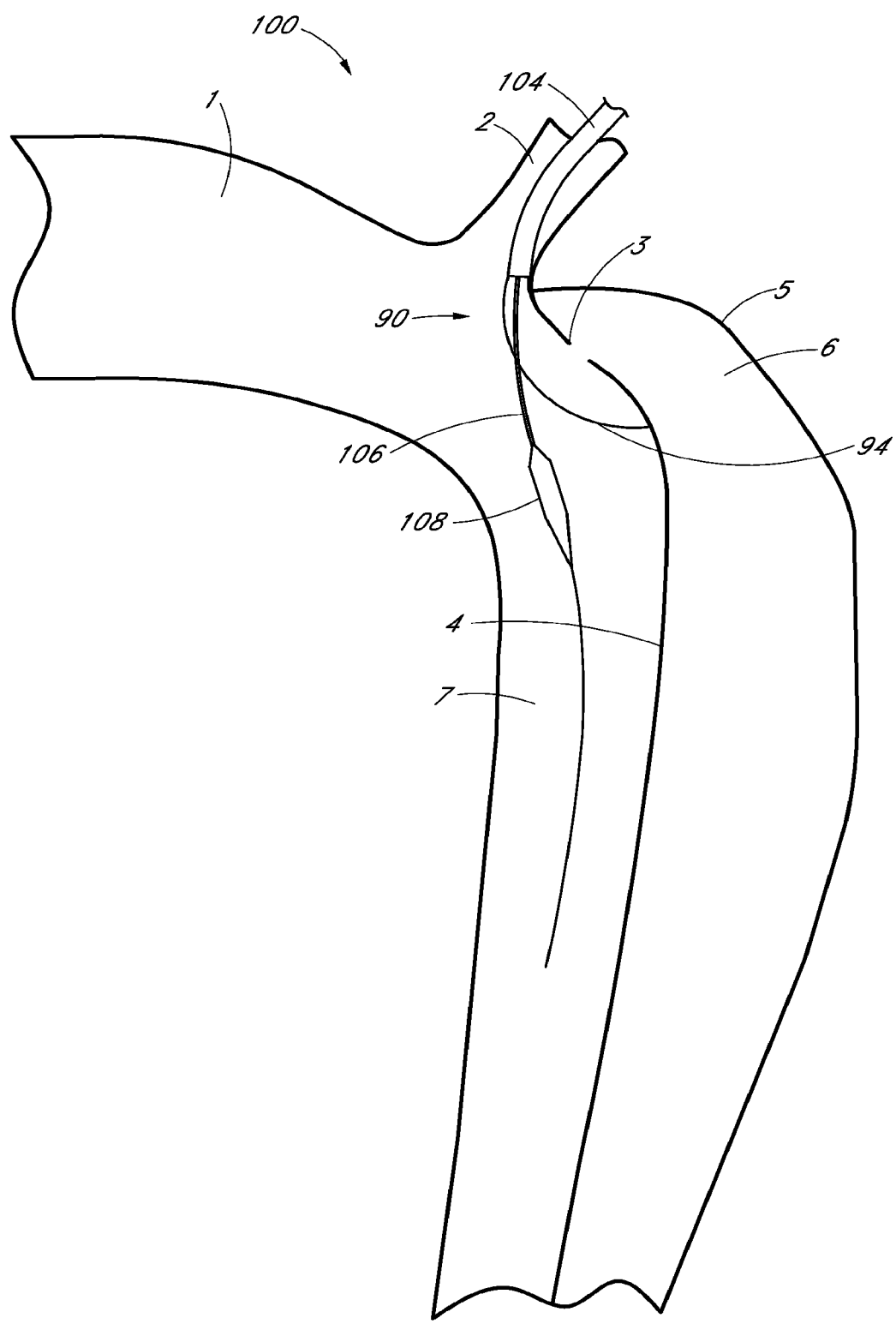
FIGS. 12 and 13 are schematic illustrations showing the embodiment of the device to treat dissections of FIG. 9B being deployed from the embodiment of the delivery catheter of FIG. 11.
Figure 13:
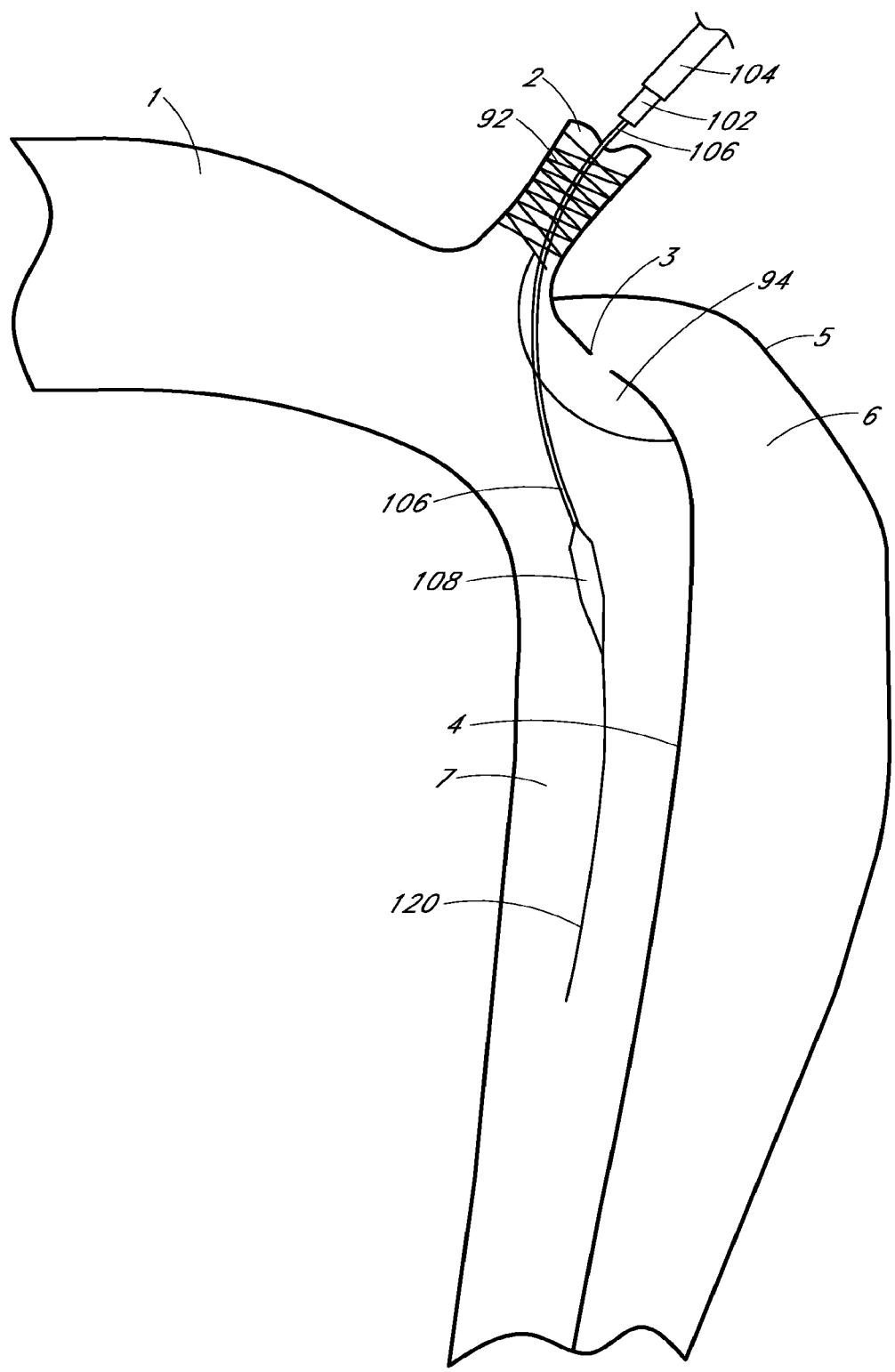
Figure 14:
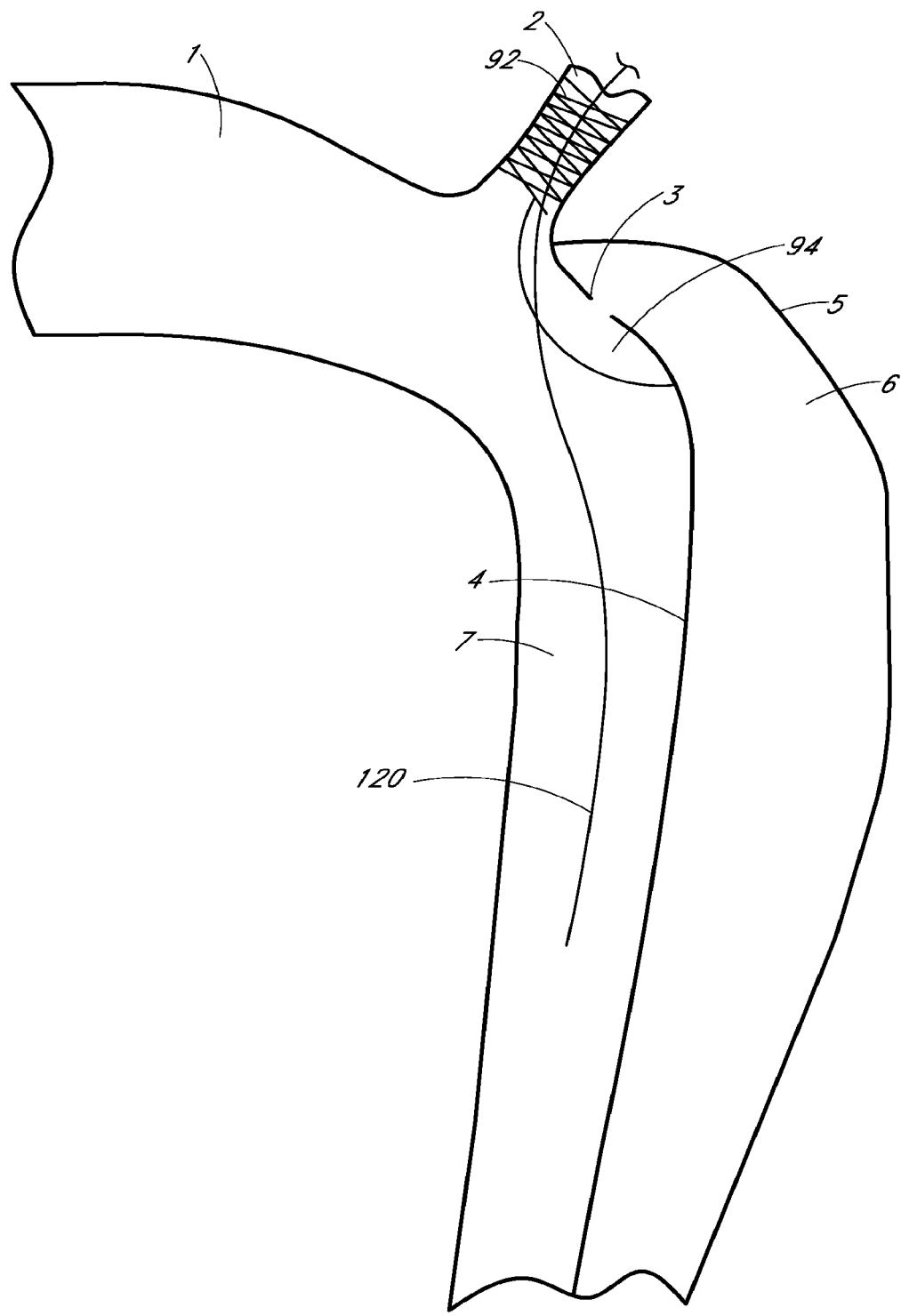
FIG. 14 is a schematic illustration showing the embodiment of the device to treat dissections of FIG. 9B deployed within the patient's vasculature.

FIGS. 12 and 13 are schematic illustrations showing the device 90 to treat dissections of FIG. 9B being deployed from the delivery catheter 100. As illustrated in FIG. 12, the cover 94 can be deployed from the delivery catheter 100 be axially retracting the outer sheath 104 relative to the tube member 106, thereby exposing the cover member 94. The delivery catheter 100 and prosthesis 90 can be properly positioned using one or more radiopaque markers supported on the delivery catheter 100 and/or prosthesis 90. Because the delivery catheter 100 was advanced through the subclavian artery 2 into the aorta 7, further axial retraction of the outer sheath 104 relative to the inner core 102 and tube member 106 can cause the anchor member 92 to be deployed from the delivery catheter 100 into the subclavian artier 2. Thereafter, the deployment catheter 100 can be axially retracted through the subclavian and radial artery and be removed from the body, as shown in FIG. 14. The guidewire 120 can thereafter be removed, leaving only the device 90 for treating dissections.

Figure 15:
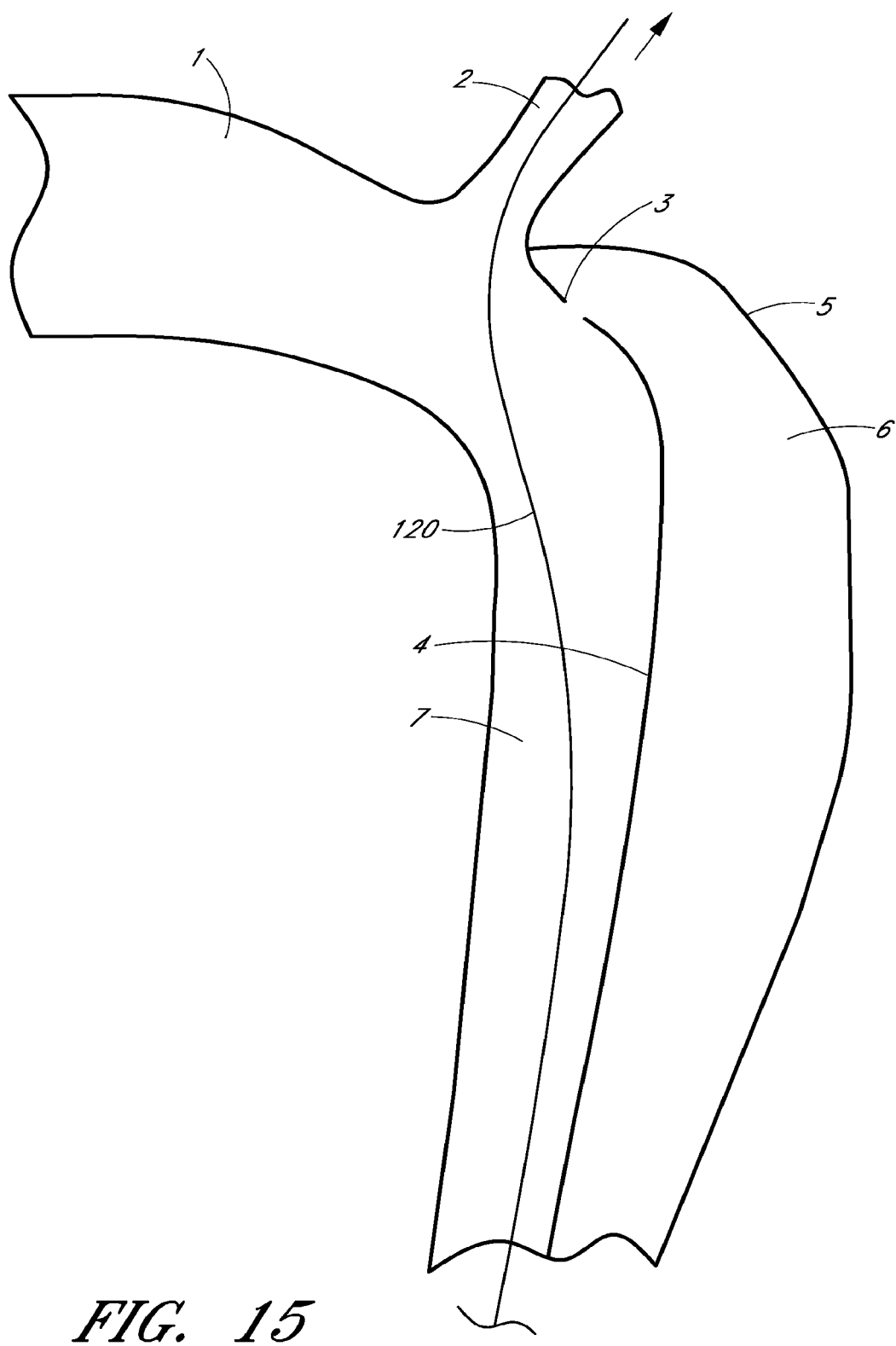
FIG. 15 is a schematic illustration of patient's aorta having a type B dissection therein, showing a guidewire being advanced through a patient's aorta into the subclavian artery.
Figure 16:
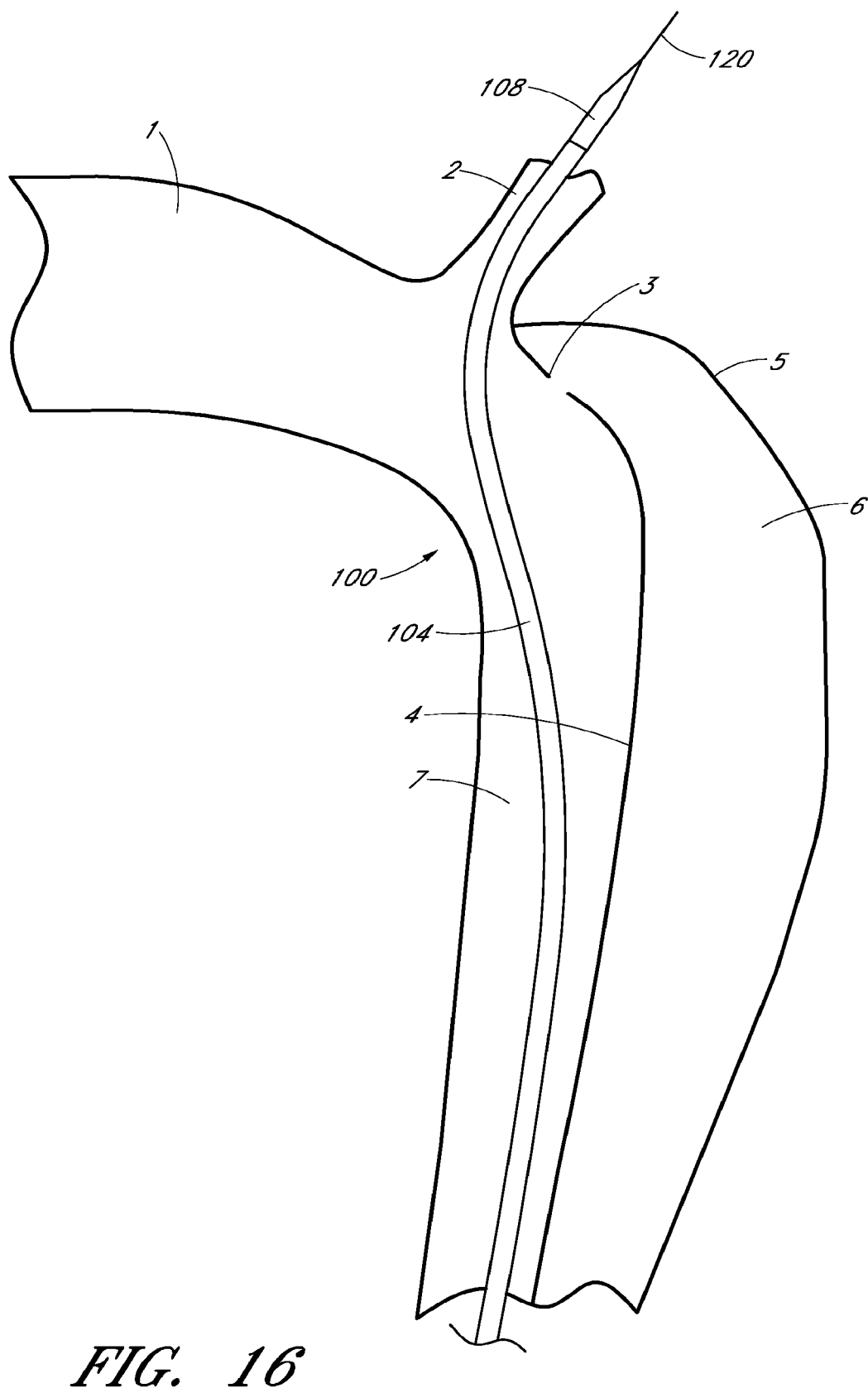
FIG. 16 is a schematic illustration showing an embodiment of a delivery catheter being advanced over the guidewire of FIG. 16.
Figure 17:
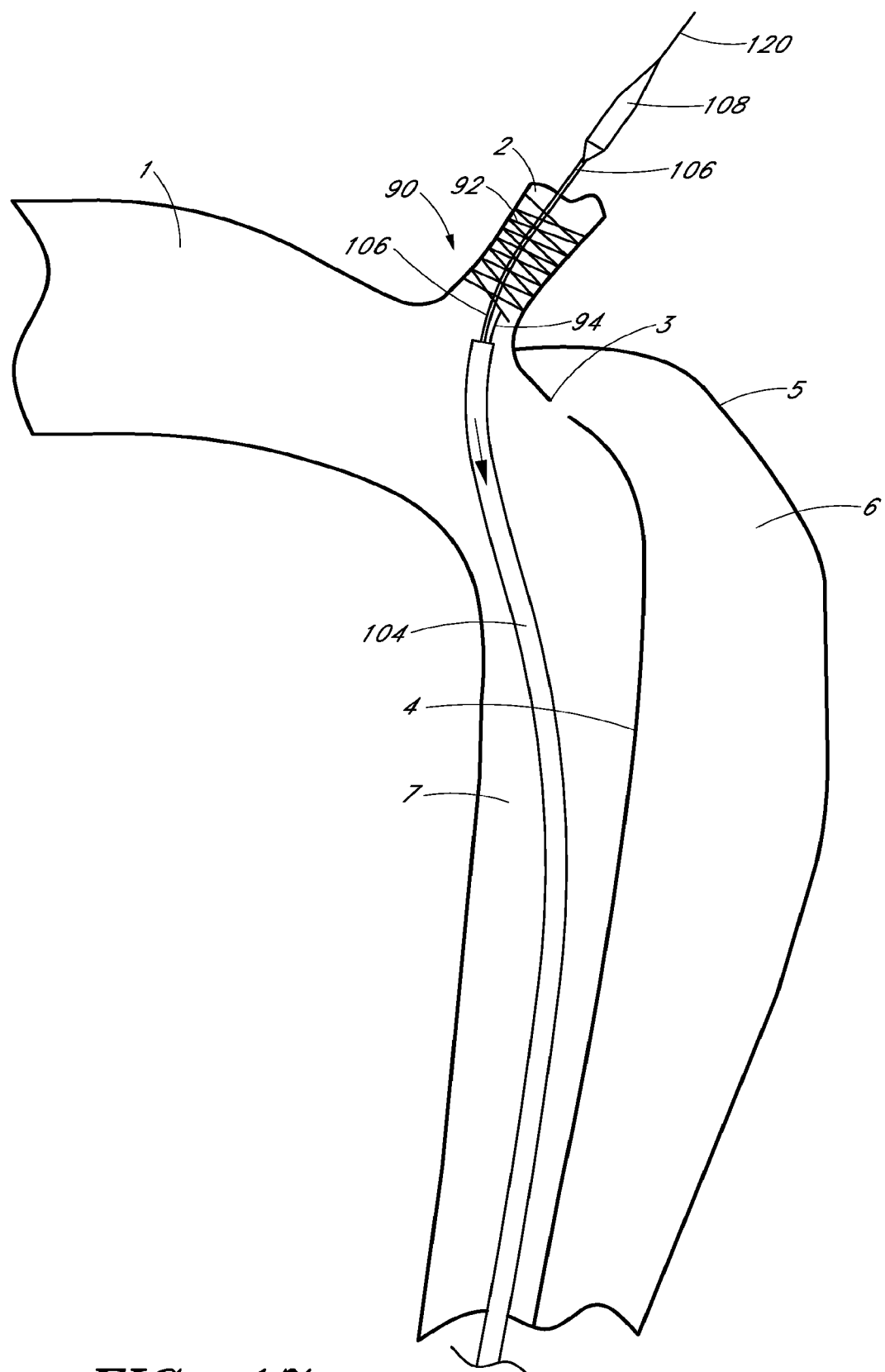
FIGS. 17 and 18 are schematic illustrations showing an embodiment of a device to treat dissections being deployed from the embodiment of the delivery catheter of FIG. 16.
Figure 18:
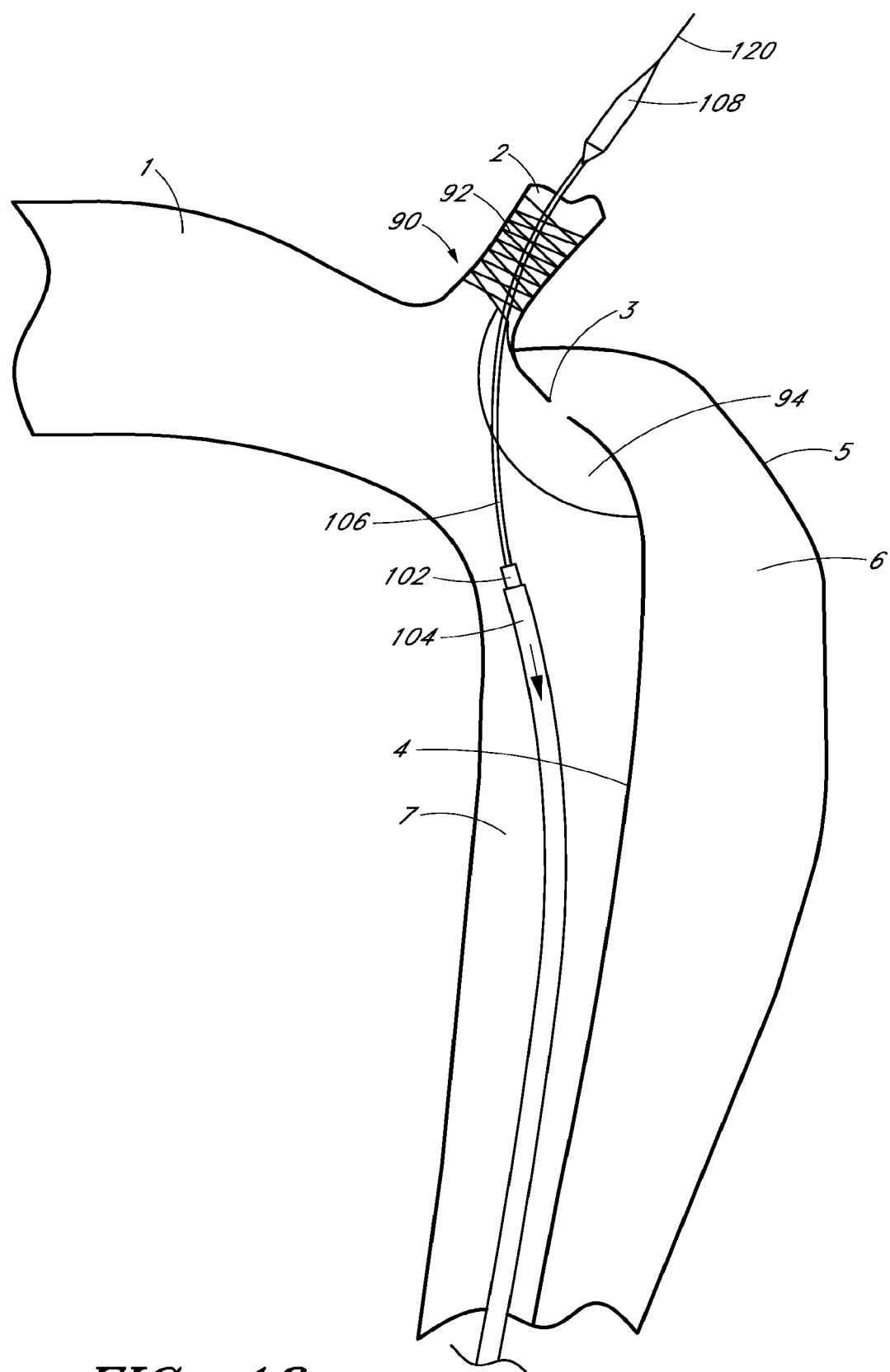

In some embodiments, the cover 94 of the device 90 can be deployed in a patient's aorta by first advancing a guidewire 120 through a patient's femoral artery into the aorta and subclavian arteries, as illustrated in FIG. 15. Thereafter, the deployment catheter 100 described above can be advanced over the guidewire 120, as illustrated in FIG. 16. Once the delivery catheter 100 has reached the target location, e.g., within the subclavian artery 2, the anchoring member 92 can be deployed within the subclavian artery 2 by axially retracting the outer sheath 104 relative to the tube member 106 and device 90, as illustrated in FIG. 17. Further retraction of the outer sheath 104 can cause the remaining components of the device 90 to be deployed within the patient's vasculature. For example, with reference to FIG. 18, further retraction of the outer sheath 104 can cause the cover member 94 to be deployed and to substantially or completely cover the entry point 3 to the dissection.

Figure 19:
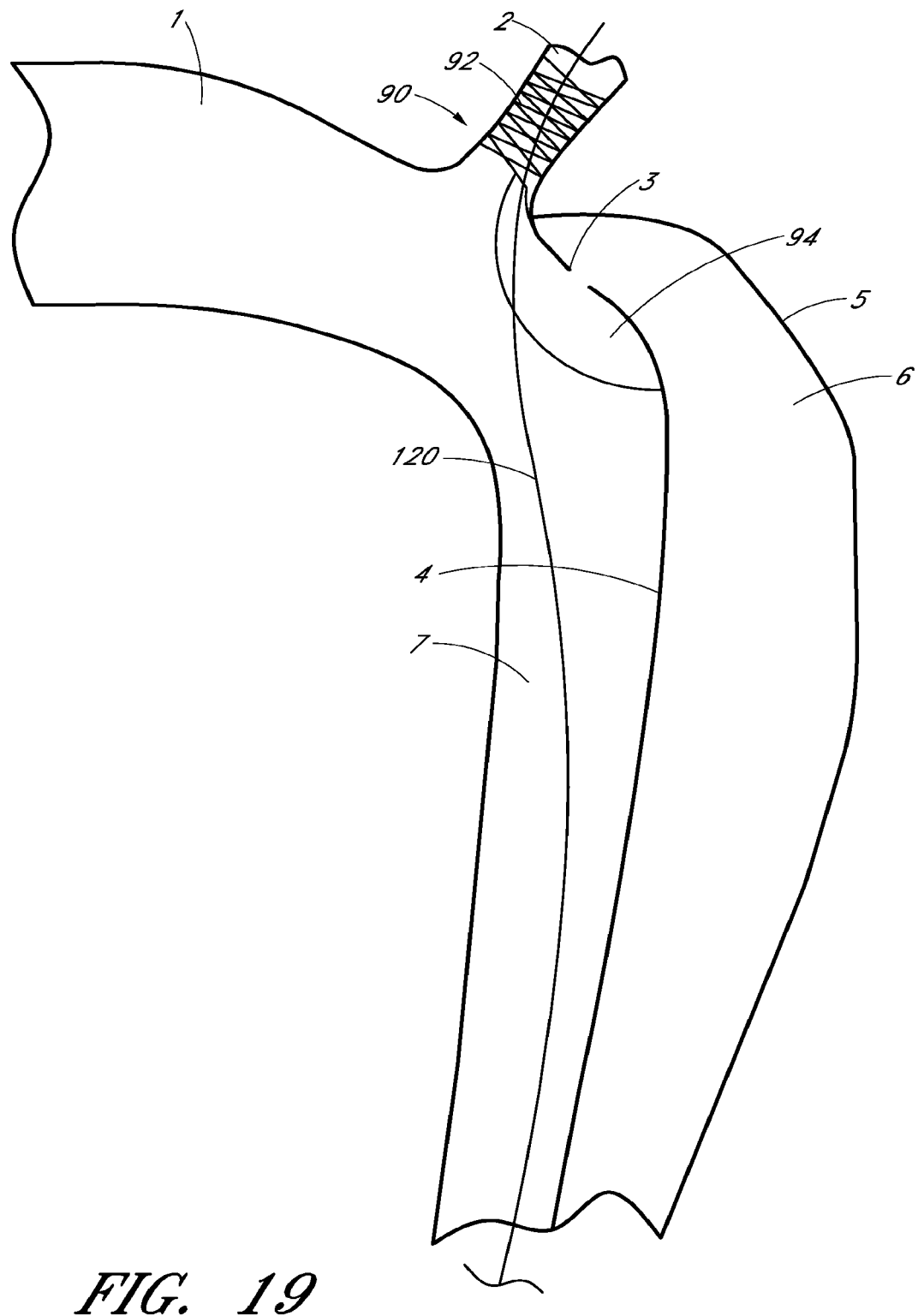
FIG. 19 is a schematic illustration showing an embodiment of the device to treat dissections deployed within the patient's vasculature.

Thereafter, the deployment catheter 100 can be axially retracted through the aorta and femoral artery and be removed from the body, as shown in FIG. 19. The guidewire 120 can thereafter be removed, leaving only the device 90 for treating dissections.

FIGS. 2-19 illustrate some embodiments of devices and methods of the present disclosure. Other embodiments that support the proposed method of entry point closure are also within the scope of the present disclosure. For example, in some embodiments, a collapsible device can be placed over the entry point and anchored to an aortic branch vessel that can be delivered with a low-profile catheter-based delivery system.

Although the inventions have been disclosed in the context of preferred embodiments and examples, it will be understood by those skilled in the art that the present disclosure extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It can be also contemplated that various combinations or subcombinations of the specific features and aspects of the embodiments can be made and still fall within the scope of the invention. Accordingly, it should be understood that various features and aspects of the disclosed embodiments can be combined with or substituted for one another in order to form varying modes of the disclosed invention. Thus, it can be intended that the scope of the present disclosure herein disclosed should not be limited by the particular disclosed embodiments described above.

What is claimed is:

1. A device for treating a vascular dissection, comprising:
   an anchoring element configured to be deployed outside of a first vessel within a second vessel in communication with the first vessel having the vascular dissection, the anchoring element having a generally tubular structure comprising a first end and a second end, the first end having a first opening into the first vessel which defines a first plane;
   a single elliptical frame that is configured to cover an entry point of the vascular dissection, a circumference of the elliptical frame being substantially coplanar with the first opening, the single elliptical frame attached to the anchoring element and configured to conform to a wall of the first vessel; and
   a cover supported by the single elliptical frame.

2. The device of claim 1, wherein the single elliptical frame is biased to deflect against the wall surrounding the entry point to the vascular dissection.

3. The device of claim 1, wherein the cover is biased to deflect against the wall surrounding the entry point into the dissection.

4. The device of claim 1, wherein the device is collapsible into a first collapsed state for positioning within a catheter and is expandable to a second expanded state.

5. The device of claim 1, wherein the anchoring element is a stent.

6. The device of claim 1, wherein the anchoring element comprises at least one of a coil, hook, barb, balloon, stent graft, screw, or staple.

7. The device of claim 1, wherein the single elliptical frame is integral with the cover.

8. The device of claim 1, wherein the cover is attached to the single elliptical frame with a fastener.

9. The device of claim 1, wherein the cover is molded onto the single elliptical frame.

10. The device of claim 1, wherein the single elliptical frame directly attached to the anchoring element.

11. A device for treating a vascular dissection, comprising:
an anchoring element configured to be deployed outside of a first vessel within a second vessel in communication with the first vessel having the vascular dissection, the anchoring element having a generally tubular structure comprising a first end and a second end, the first end having a first opening into the first vessel; and
a single elliptical frame that is configured to cover an entry point of the vascular dissection, and conform to a wall of the first vessel; and
a cover supported by the single elliptical frame,
wherein the first end of the anchoring element is attached to the elliptical frame such that the first opening is positioned between a proximal end and a distal end of the elliptical frame.

12. The device of claim 11, wherein the device is configured such that when deployed, the first opening is positioned between the proximal end of the elliptical frame and an entry point of the dissection.

13. The device of claim 11, wherein the frame further comprises a central strut connected to both proximal and distal ends of the elliptical frame.

14. The device of claim 13, wherein the first end of the anchoring element is attached to the central strut.

15. A device for treating a vascular dissection, comprising:
an anchoring element configured to be deployed outside of a first vessel within a second vessel in communication with the first vessel having the vascular dissection, the anchoring element having a generally tubular structure comprising a first end and a second end, the first end having a first opening into the first vessel;
a single elliptical frame that is configured to cover an entry point of the vascular dissection,
the single elliptical frame being configured to conform to a wall of the first vessel; and
a cover supported by the single elliptical frame,
wherein the first end of the anchoring element is attached to the elliptical frame such that the first opening is directly attached to a proximal end of the elliptical frame.

* * * * *